(12) United States Patent
Glazman

(10) Patent No.: US 6,328,937 B1
(45) Date of Patent: Dec. 11, 2001

(54) APPARATUS FOR KILLING MICROORGANISMS

(76) Inventor: Mark Glazman, 2725 Floribunda Dr., Columbus, OH (US) 43209

( * ) Notice: Subject to any disclaimer, the term of this patent is extended or adjusted under 35 U.S.C. 154(b) by 0 days.

(21) Appl. No.: 09/427,847

(22) Filed: Oct. 26, 1999

(51) Int. Cl.[7] ........................... B01J 19/08
(52) U.S. Cl. ............... 422/186.3; 422/121; 422/24
(58) Field of Search ................. 422/186.3, 121, 422/24

(56) References Cited

U.S. PATENT DOCUMENTS

| | | |
|---|---|---|
| 5,112,370 | 5/1992 | Gazzano . |
| 5,200,156 | 4/1993 | Widekamp . |
| 5,589,132 * | 12/1996 | Zippel .................... 422/121 |
| 5,612,001 | 3/1997 | Matschke . |
| 5,616,172 | 4/1997 | Tuckerman et al. . |
| 5,635,133 | 6/1997 | Glazman . |
| 5,833,740 | 10/1998 | Brais . |
| 5,925,320 * | 7/1999 | Jones .................... 422/121 |

* cited by examiner

*Primary Examiner*—Kishor Mayekar

(57) ABSTRACT

An apparatus for killing microorganisms in a primary flow of a fluid medium using germicidal beams to kill microorganisms in a portion of the primary flow of the fluid medium has a housing having an inlet end 1 and an outlet end 4. The housing 20 has reflective inner surfaces 2R, 3R, 5R and 6R along the path 100 of the germicidal beams, a source 30 of germicidal beams located in the housing 20 and at least one baffle 40 located near the source 30 of the germicidal beams. The baffle 40 projects from an inner surface 6 of the housing 20 and is configured to converge the primary flow of air into the germicidal beams path in close proximity to the germicidal beams source 30. The at least one baffle 40 has an upstream portion 41 lying substantially out of the beam path 100 and a downstream portion 42 lying in the beam path 100.

8 Claims, 4 Drawing Sheets

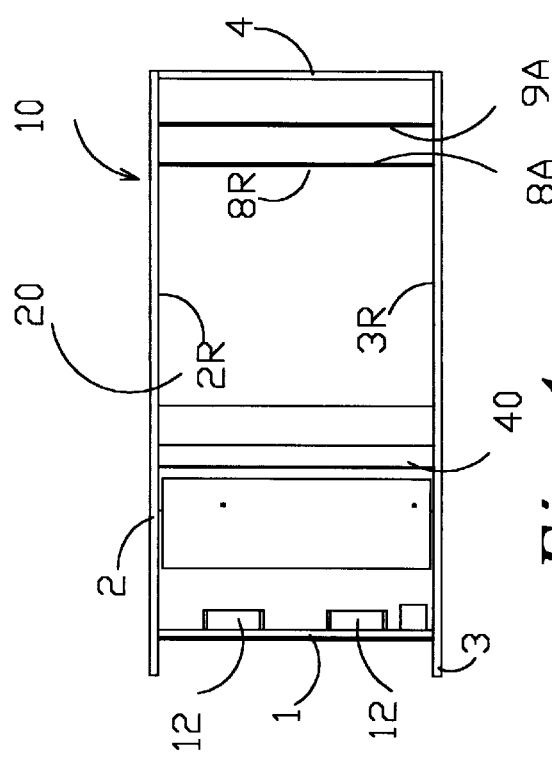
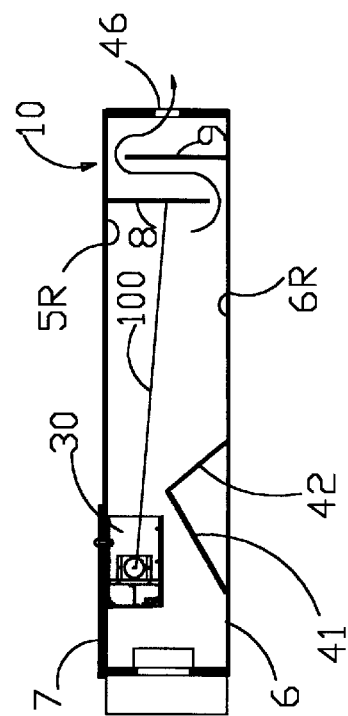

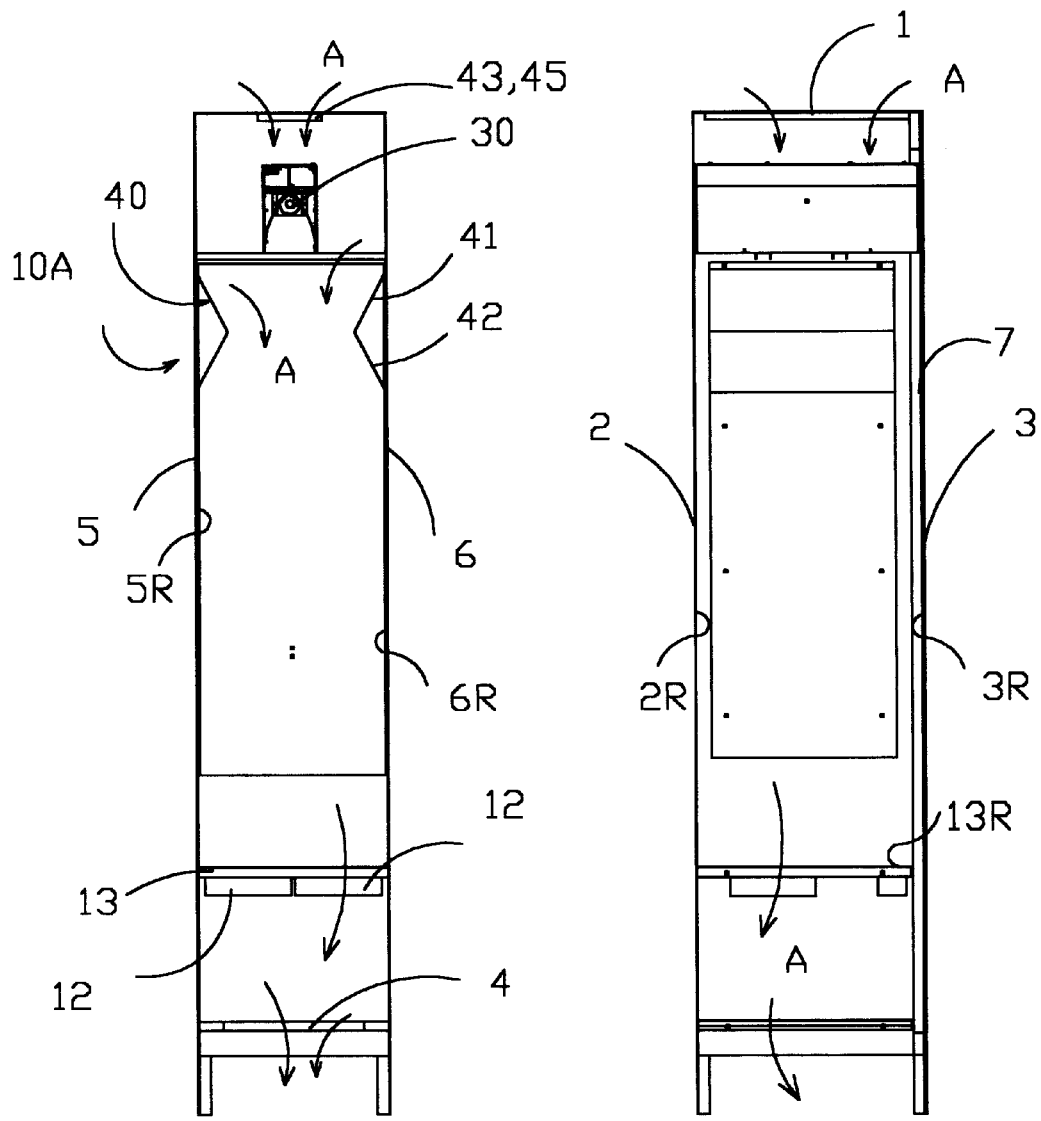
*Fig.4*   *Fig.5*
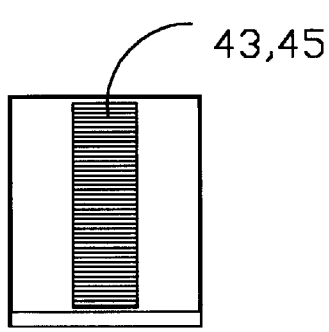
*Fig.6*

APPARATUS FOR KILLING MICROORGANISMS

FIELD OF THE INVENTION

The present invention relates to fluid purification and in particular sterilization by irradiation with an ultraviolet radiation source.

BACKGROUND OF THE INVENTION

The airborne transmission of bacteria and viruses, chiefly respiratory disease organisms is a serious problem in health care. The control of airborne disease transmission has become increasingly important with an increasing number of people growing older with weakened immune systems more vulnerable to airborne disease or infected with human immunodeficiency virus (HIV) or other airborne and difficult to cure diseases. This coupled with antibiotic resistant strains of bacteria have created a need for inexpensive, efficient air purification systems. The spread of air born infections can be reduced by killing the infectious microorganism by ultraviolet (UV) radiation. Ultraviolet radiation to destroy airborne microorganisms can be used in ceiling fixtures suspended above the people in the room or inside ventilation system air duct.

The continuing spread of tuberculosis (TB) infection and other airborne disease in modern health institutions, correctional institutions, and shelters for homeless indicates however, that the known air purification systems are inadequate in controlling the spread of airborne microorganisms.

An other important field where the spread of microorganisms needs to be controlled is liquid, and particularly water-based solutions.

The sterilization by ultraviolet radiation has been known more than fifty years. Various methods and apparatus have been invented for ultraviolet irradiating fluids, air and water in particular, in order to control the spread of microorganisms by destroying those microorganisms with a sufficient dose of radiation.

Air purification by means of filtration and irradiation is widely practiced. Conventional air cleaning systems commonly have a filtration and irradiation units. Irradiation is placed after filtration because the ultraviolet lamps used as a source of the radiation readily attract dust which can accumulate on a surface of the lamp, block the UV radiation inside the lamp and interfere with their germicidal effect.

Commonly irradiation is placed before humidification because ultraviolet radiation is most effective in an atmosphere with relative humidity less than 70% which promotes oxidation. Ultraviolet germicidal radiation has been proven to be more effective and economically feasible than any other approach to reducing the number of microorganisms in the liquid or gas flow.

Conventional UV fluid sterilization systems have relied on exposure of suspended microorganisms to ultraviolet radiation by passing medium over or around one or more ultraviolet lamps. This method is used in U.S. Pat. Nos. 5,112,370 and 5,200,156. This method has a number of shortcomings.

The first shortcoming of the previous art is their low reliability. The particles suspended in the fluid accumulate on the surface of the lamp or protective tubes, forming the UV light absorption layer, which restricts or eliminates the germicidal effectiveness. The reliability and actual germicidal effectiveness depend on the quality of the medium filtration and come very small and unpredicted if the medium is unfiltered or poorly filtered.

The second shortcoming of previous art of UV sterilization systems is that they have low efficiency of use of the UV energy, because their lamps accumulate particles on the surface from the beginning and because in ducts or pipes with ratio length-L to diameter-D L/D=10:1 only 6% of beams have their path length equal to the longest available way (L/2 that is when the lamp is placed halfway between the longest straight line length of the duct (L), the maximum available way is only L/2), other beams, 94% are directed on much shorter paths and could irradiate smaller volume on its way, and, hence, are less efficient.

The third shortcoming of previous art is nonuniform irradiation intensity in an irradiated volume. In the device for sterilization according to U.S. Pat. No. 5,200,156 the author tried to achieve more uniform irradiation intensity than before by applying a flat oval cross section light source with or without the reflectors. But this invention made limited progress because the according to the U.S. Pat. No. 5,200,156 can irradiate towards axis of pipe only 50% of radiation and only 6% of the beams will have length equal to the length of the longest available way. Other beams are short slanting beams. They irradiate smaller volume than longest beams and are absorbed by the pipe walls. Due to the early absorption, the efficiency of the use of short slanting beams is very low. As a result the efficiency of all previous art, including the sterilizer according to U.S. Pat. No. 5,200,156 is too low.

The fourth shortcoming of previous art according to U.S. Pat. No. 5,200,156 is that the sources of radiation are installed inside the medium flow, liquid or gas, and create a substantial pressure loss in the system. To retrofit an operating ventilation or other system with known UV sterilization system it is necessary to replace a fan, pump, electric motor by more powerful equipment.

In U.S. Pat. No. 5,635,133, the above mentioned shortcomings were eliminated by an apparatus invented by Dr. Mark Glazman that increased the efficiency of the germicidal radiation for killing microorganisms by first providing a secondary flow of particle free fluid that maintained the surfaces of the means for transferring and orienting the germicidal beams free of energy absorbing dust particles and by secondarily orienting the germicidal beams of radiation into an array of parallel beams which when passed though a duct containing a primary flow of fluid medium achieved a very high efficiency due to the orientation of the beams being generally parallel to the duct path.

This apparatus utilized an ultraviolet lamp and a substantially parabolic reflector to achieve these improvements in combination with other elements.

A feature of this design was the ability to place the UV lamp at one end of the duct and direct the array of beams along the path of the flow of the primary medium.

While this invention of Dr. Glazman has demonstrated a dramatic increase in germicidal efficiency particularly in the area of air purification in ducted ventilation systems, further developments have been discovered that can increase the efficiency even further.

The first Glazman air purification system relied on a straight portion of ducting to achieve a microorganism killing zone or path. This path was preferably about 3 meters in length, the longer the better.

In many applications, the length available to create a killing path may be substantially less than 3 meters, often 2 meters or less is available in which the germicidal effect must be achieved. The problem is how to efficiently and safely create a highly effective kill zone in a very short duct.

In many applications, both residential and commercial, there simply is no available central ducting to be used. In these situations, the apparatus for killing microorganisms must be capable of providing its own flow path of fluid medium. In these cases, the apparatus may have a very short flow path available in which to kill the microorganisms.

In such a case a self contained device is needed. In U.S. Pat. No. 5,112,370 by Michele Gazzano of Milan, Italy, a Device for Sterilizing a Forced Air Flow by Means of Ultraviolet Radiation, discloses an elongated housing provided with reflecting inner surfaces accumulating an ultraviolet radiation source and a fan for sucking air into the device and sending it out after being subjected to ultraviolet radiation in an air flow passage. The reflective surfaces were formed in an optical labyrinth with a plurality of parallel and spaced sheets defining paths for the air flow and shielding and absorbing the ultraviolet radiation to prevent escaping thereof outside the device.

The Gazzano device as disclosed shows the cylindrical UV lamp's orientation as being parallel to the air flow path. Accordingly the UV beams had to be deflected at an angle of about 150 degrees off of numerous reflective surfaces in order to achieve any meaningful killing zone. The reflective surfaces further included the internal surfaces of the housing which also were perpendicular to the beam paths. The entire length of the killing zone was limited effectively to the length of the UV lamp. To compensate for this shortcoming the Gazzano device employed four parallel lamps this enables the device to become wider and accordingly could accommodate more air. A primary limitation of this device was the requirement that multiple lamps were needed. It is readily appreciated that the apparent effective kill zone on a per lamp basis was limited to about a distance of 2 to 3 times the diameter of the UV lamps glass envelope. This is an easily recognized limitation of the use of lamps wherein the beam is directed perpendicular to the air flow.

In the present invention it is an objective to use an Ultra violet lamp as a means for killing microorganisms, hereinafter referred to as a source of germicidal beams.

It is a further objective to provide an apparatus, which includes the ultra violet lamp, the apparatus providing a way in which the germicidal beams are more efficiently used in a very short length of a germicidal killing zone.

It is a further objective that the apparatus substantially blocks the escape of all the radiation emitted by the UV lamp.

It is a further objective to maintain the orientation of UV lamp so that the beams are directed substantially along the same direction as the fluid medium path.

It is a further objective of the invention that the device can achieve an efficient kill rate with as few as one UV lamp.

It is still a further objective that the apparatus be fully self contained only requiring an electrical connection to provide power to the UV lamp, its ballast and any fans and motors if used to provide an air flow.

SUMMARY OF THE INVENTION

An apparatus for killing microorganisms in a primary flow of a fluid medium using germicidal beams as a means for killing microorganisms in a portion of the primary flow of the fluid medium is disclosed. The apparatus, 10, 10A has a housing 20 having an inlet end 1 and an outlet end 4. The housing 20 has reflective inner surfaces 2R, 3R, 5R and 6R along the path 100 of the germicidal beams, a source 30 of germicidal beams located in the housing 20 and at least one baffle 40 located near the source 30 of the germicidal beams. The baffle 40 projects from an inner surface 6 of the housing 20 converging the primary flow of air into the germicidal beams path in close proximity to the germicidal beams source 30. The at least one baffle 40 has an upstream portion 41 lying substantially out of the beam path 100 and a downstream portion 42 lying in the beam path 100.

The source 30 of germicidal beams preferably also has a means for directing and orienting the beam path. In one embodiment this means for directing and orienting the beam path 100 is an device 50, the device 50 having substantially parabolic reflector 60.

The reflective surfaces 2R, 3R, 5R and 6R have a mirror like reflection and the radiation intensity adjacent to the outlet 4 is 50 percent or greater at a distance of 1 meter or less from the source, the radiation intensity at a distance 0.25 m from the source being 100%.

In a preferred embodiment the germicidal source 30 is an ultra violet radiation lamp 32 having a cylindrical glass envelope 34, a portion of the glass envelope 34 has a means 36 for directing and orienting the germicidal beams. This means 36 is a reflective coating longitudinally encircling approximately one half or less of the surface of the glass envelope. This reflective coated lamp 32 in the most preferred embodiment is used in combination with the device 50, the device 50 has a substantially parabolic shaped reflector 60 for orienting and directing the beam path 100. This parabolic reflector 60 has an aperture 44 for allowing a secondary flow of particle free air to flow over the glass envelope 34 and the reflective surface of the parabolic reflector 60 thus keeping these components clean and dust free. The aperture 44 in the parabolic reflector 60 is preferably is aligned relative to the reflective coating 36 of the lamp 32 such that the emission of germicidal beams that otherwise would have passed back through the aperture 44 are instead reflected back toward the outlet end 4 of the housing 20 directly into the primary flow A.

BRIEF DESCRIPTION OF THE DRAWINGS

The invention will now be explained by way of examples and with reference to the following drawings, it being appreciated that like components used in the various examples will have the same reference numerals for ease of understanding.

FIG. 1 is a schematic view of the apparatus shown in a front view;

FIG. 2 is a schematic side view of the apparatus;

FIG. 3 is a schematic bottom view of the inlet end of the apparatus;

FIG. 4 is a schematic front view of a second alternative apparatus;

FIG. 5 is a side view of the second alternative apparatus according to the invention;

FIG. 6 is a top view of the second alternative apparatus;

DETAILED DESCRIPTION OF THE INVENTION

Figure 7:
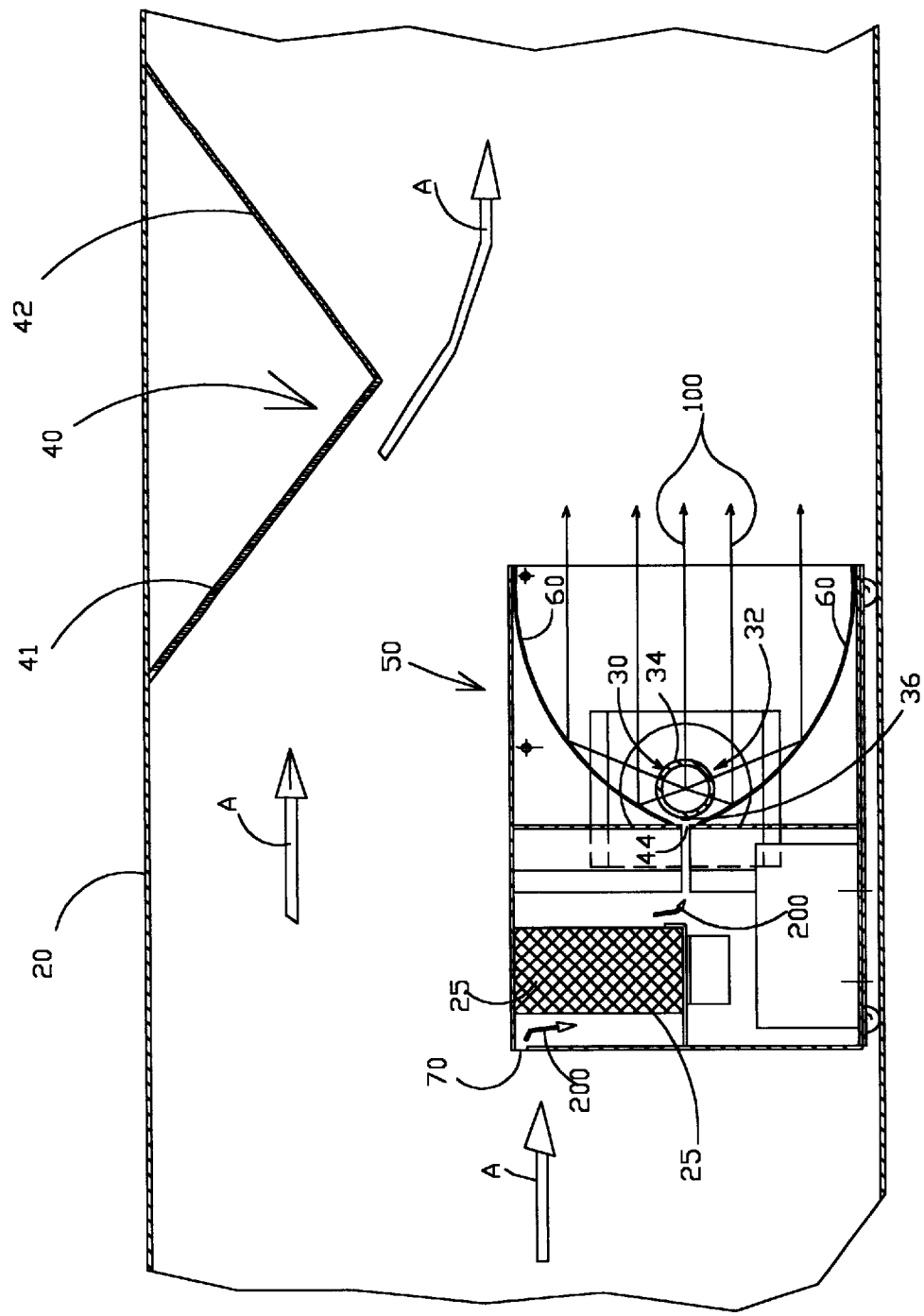
FIG. 7 is a portion of the apparatus first preferred embodiment having a device 50 with a germicidal beam source 30; wherein the reflective coating 36 of the lamp is aligned with the aperture 44 of the means for directing and orienting the beam path 100.

With reference to FIG. 1 through FIG. 3, the apparatus 10 according to the invention is shown in schematic views. The apparatus 10 has a housing 20 having an inlet end 1 and an outlet end 4 for intaking and exhausting a primary flow of air A.

In FIGS. 1 through 3, the inlet end 1 is located at the bottom of the housing 20 while the outlet end 4 is located at the top of the housing. In this embodiment, the primary air flow will come in from the floor level and after treatment will be exhausted from the top at the outlet end 4.

As shown, the air is drawn into the housing 20 by means of one or more fans 12. Preferably, the fans 12 are driven by electric motors. In applications where noise must be minimized, these fans 12 are generally small and very quiet. As illustrated, the fans for a room unit type apparatus 10 have an air output of about 100 CFM. This output of air flow is sufficient to circulate enough air to purify a large room (12' by 15' or greater) very efficiently.

As illustrated, the housing 20 is made substantially rectangular having four sides 2, 3, 5, 6, in addition to the ends 1, 4. Each of the four sides 2, 3, 5 and 6 have reflective interior surfaces 2R, 3R, 5R and 6R. These reflective surfaces are positioned in the region of the housing wherein the germicidal beam path 100 radiates.

As illustrated, near the outlet end 4 of the housing 20 is a first shield 8 and a second shield 9. These shields have openings that are juxtaposed, which allow the treated primary flow to be exhausted through a vent 46. The interior surface 8R can be reflective while the surface 8A, and 9A of the second shield 9, can be black or light absorbing. This, in combination with the positioning of the openings in the shields 8, 9, insures that no harmful UV radiation escapes the housing 20.

In the apparatus 10, the side 5 further includes a door 7. In apparatus 10 the door 7 may preferably include a lock requiring a key for access and an electrical interlock switch commonly found on refrigerator doors. These features, although not illustrated, precludes opening the door while the germicidal UV lamp 32 is on.

Attached to the door 7 is a means for killing microorganisms including germicidal source 30. The source 30 as shown includes a germicidal UV lamp 32 connected to electrical receptacles, which in turn can be connected to an electrical power source.

The source 30 as shown can be one of the devices shown in FIGS. 7 and 8 which are discussed in detail later.

In apparatus 10, the germicidal beams are oriented and directed in a beam path 100. This beam path is directed germicidally toward the outlet end 4 of the apparatus10. Located along the side 6 of the apparatus 10 is a baffle 40. The baffle 40 includes a first or upstream portion 41 lying substantially outside the beam path 100 and a secondary downstream portion 42 lying in the beam path 100. The portion 41 and 42 in combination create the baffle 40 which redirects the primary air flow A, converging the air flow A directly in front of the germicidal killing means 30. This channeling of the primary air flow A insures that all the primary air A is exposed to the maximum radiation intensity as it passes over the baffle 40. The portions 41, 42 can be made from a single sheet of material, which is bent, or two different materials. It is believed beneficial if the downstream portion 42 is made of or has a reflective surface material similar to the sidewalls 2R, 3R, 5R, 6R and 8R of the shield 8. In this way, the germicidal beam 100 retains a higher radiation intensity from the beam source 30, the lamp 32 to the shield 8R at the outlet. This is so because with all the sidewalls 2R, 3R, 5R, and 6R and 8R of the shield 8 being reflective along the beam path 100 means that the energy that would otherwise be absorbed in the walls is now bounced back into the air flow A.

In FIGS. 4 through 6 is a schematic view of an alternative second embodiment apparatus 10A. In this apparatus 10A, the inlet side 1 is at the top end of the apparatus and the germicidal source 30 for killing microorganisms is located at this inlet end of the apparatus. The fans 12 are located at a floor level outlet side 4. The fans 12 are oriented to suck the primary air flow A though the top of apparatus 10A and expel it after treatment at the end 4 near the floor as illustrated.

In this unit or apparatus 10A, the germicidal source 30 is located somewhat centrally near the inlet end 1. On each side 5 and side 6 a baffle 40 projects. The baffles 40 each have a downstream portion 42 lying substantially in the beam path 100 and an upstream portion 41 lying substantially outside the beam path 100. The combination of baffles redirect the air flow A converging in directly in front of the germicidal source 30 which as in the other embodiment is preferably a cylindrical UV lamp 32.

The inlet end 1 preferably includes an inlet vent 43 that is small enough to limit back skatter of UV light emitted from the apparatus 10A. As in the apparatus 10, the sides 2, 3, 5 and 6 of apparatus 10A are covered or coated with a reflective surface 2R, 3R, 5R and 6R.

The fans 12 are attached to a panel 13. The panel 13 has an opening for each fan and may have a reflective surface 13R. Bounce back of the beam 100 is blocked from the inlet end 1 vent 43 by the baffles 40 and the source 30.

In both apparatus an air intake particulate filter 45 may be used to limit the amount of dust entering the apparatus 10, 10A.

As in the other apparatus, the second embodiment may in include a door 7. In this apparatus 10A, the door 7 may extend almost the full length of the apparatus, providing an access to radiation source and the fans for maintenance.

With reference now to FIG. 7, the germicidal source 30 for killing microorganisms includes a device 50.

The device 50 as shown is fully disclosed in PCT application PCT/US96/13417 which is incorporated herein by reference in its entirety.

The device 50 has an opening 70 for receiving a secondary flow 200 of air from the primary flow of air A. This secondary flow then passes through a filter 25 in the device 50. This filtered secondary flow 200 then passes through an aperture 44 of a substantially parabolic reflector 60. This secondary air flow 200 then surrounds the reflective surfaces of the parabolic reflector 60 and a germicidal source of beams 30, the source 30 being a cylindrical UV lamp 32 having a glass envelope 34. The lamp 32 is located centered preferably at the focal point of the parabolic reflector 60.

Figure 8:
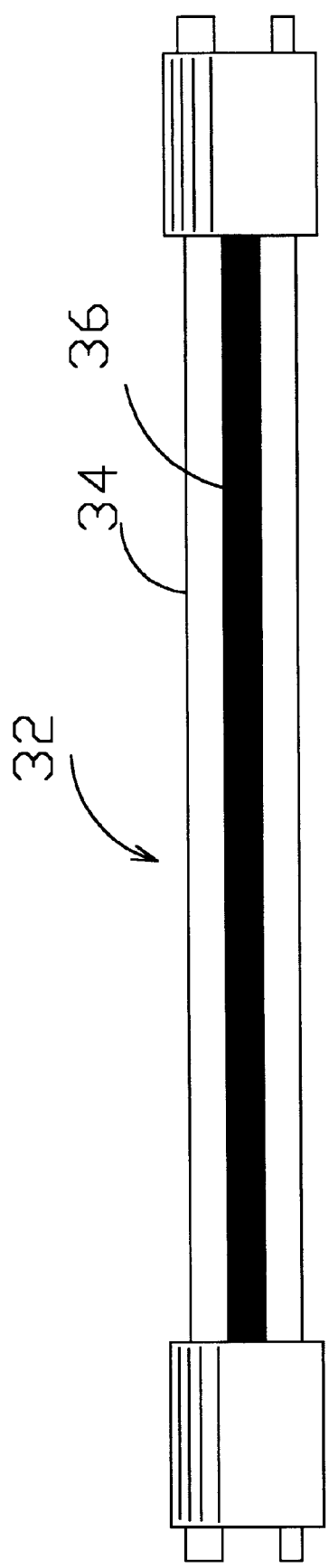
FIG. 8 is a second preferred embodiment wherein the germicidal beam source is a UV lamp 32 with a reflective coating 36.
Figure 10:
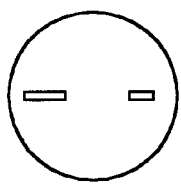
FIG. 10 is an end view of a UV lamp 32 of FIG. 8.

The source of the germicidal beams 30 may be the UV lamp 32 as shown in FIG. 8. This lamp 32 includes a cylindrical glass envelope 34 with a means 36 for directing and orienting the germicidal beams. The means 36 preferably is a reflective coating 36 longitudinally encircling approximately one half or less of the surface of the glass envelope.

In such an application, this lamp 32, having the reflective coating 36, is simply placed in a receptacle having electrical connectors that insure the lamp's beam path 100, is fixed along the flow path A. This can be accomplished by means of two or more connector pins or by corresponding flats in the receptacle ends and the lamp ends insuring the proper angular orientation for the lamps 32 as illustrated in FIG. 8. This lamp, 32 is the subject of a related copending patent application filed the same day as this application, entitled An Improved Germicidal Ultraviolet Lamp.

Figure 9:
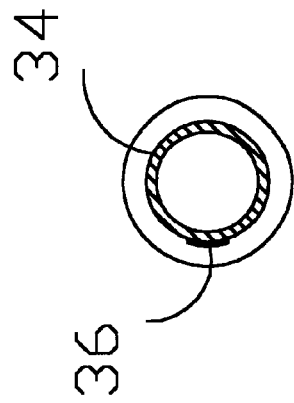
FIG. 9 is a cross-sectional view of a UV lamp 32 of FIG. 8.

Most preferably the reflective coated lamp 32 is used in combination with the device 50, such that the apparatus 10 or 10A has the aperture 44 of the parabolic reflector 60 aligned with the reflective coating 36 on the envelope 34 as shown in FIG. 9. In this embodiment the lamp 32 insures that the beam emission that would have been lost by passing through the aperture 44 is reflected into the primary airflow A, thus contributing to the germicidal beam intensity. This simple coating prevents the about 10 degrees of the 360 degrees of beam emission to be saved. This in combination with the reflector 60 insures about 100% of the emission is directed into the primary flow path A.

It is believed that the reflective coatings or surfaces should be polished aluminum, or other materials, which have a high level of UV reflectivity for maximum efficiency.

When aluminum highly polished surfaces were tested the radiation intensity at the baffles 40 was measured. This intensity at the distance 0.25 m from the source was set at 100%. At a distance of 1 meter, the intensity was maintained greater than 50% preferably. For comparison, when the prior art unit disclosed in U.S. Pat. No. 5,635,133 was placed in a heating duct, the loss was greater than 80% at 1 meter or greater due to the energy absorbing dust on the surface of the ducts. While this seems like a relatively large loss in the prior art unit, it must be appreciated that it has the advantage of lengths of about 3 meters or more to purify the air flow. The apparatus of the present invention when constructed as a room air purification device has less than 2 meters, more typically, as in apparatus 10A, one meter or less. Accordingly these units simply must be more efficient in a shorter length. Assuming even higher powered UV lamps are developed, it can easily be appreciated that the design of the housings 20 can play an important beneficial contribution to the efficacy of the system. The baffles 40 when positioned as shown, limit the amount of reflective backscatter that can occur in addition to channeling the air flow A into the highest portion for the germicidal radiation intensity. This in combination with the highly reflective surfaces enable the downstream efficiency to be more than twice as efficient at a distance of one meter from the source 30 than standard ducting without baffeling or reflective surfaces.

When coupled with specially designed lamps 32 having a reflective coating 36, the efficiency is about 3 times greater than the prior art systems.

These efficacy improvements enable small room style UV air purifiers to be used with sufficient bacterial killing power to achieve an environment that provides meaningful relief from allergies caused by mold, spores as well as bacterial and viral infections. An unlike conventional HEPA air purification device's filter must be replaced every 2 months or less to maintain efficacy, whereas, the UV's lamp life and filtration efficacy is at least 1 year.

What is claimed is:

1. An apparatus for killing microorganisms in a primary flow of a fluid medium using germicidal beams as a means for killing microorganisms in a portion of the primary flow of the fluid medium, the apparatus comprising:
   a housing having an inlet end and an outlet end the housing having reflective inner surfaces along the path of the germicidal beams;
   a source of germicidal beams located in the housing and at least one baffle located near the source of the germicidal beams, the baffle projecting from an inner surface of the housing configuring to converge the primary flow into the germicidal beam path in close proximity to the germicidal beam source; and
   wherein the source of germicidal beams has a means for directing and orienting the beam path upstream in the primary flow toward one of either the inlet end or the outlet end.

2. The apparatus of claim 1, wherein the at least one baffle has an upstream portion lying substantially out of the beam path and a downstream portion lying in the beam path.

3. The apparatus of claim 1, wherein the means for directing and orienting the beam path is a device, the device having a substantially parabolic reflector having a reflective surface.

4. The apparatus of claim 3, wherein the reflective surface has a mirror reflection and the radiation intensity at the distance of 1 meter from the source is 50 percent or greater than the radiation intensity at the distance 0.25 meter from the source.

5. The apparatus of claim 3, wherein the substantially parabolic reflector has an aperture and the source is an ultraviolet radiation lamp having a glass envelope, a portion of the glass envelope has the means for directing and orienting the germicidal beams, the means being a reflective coating longitudinally encircling approximately one half or less of the surface of the glass envelope, wherein the aperture of the parabolic reflector is aligned with the reflective coating of the glass envelop of the lamp.

6. The apparatus of claim 1, wherein the germicidal source is an ultraviolet radiation lamp having a glass envelope, a portion of the glass envelope has the means for directing and orienting the germicidal beams, the means being a reflective coating longitudinally encircling approximately one half or less of the surface of the glass envelope.

7. The apparatus of claim 1 wherein the housing has a floor level end and a top end, the inlet end being near the floor level end and the outlet end being near the top end.

8. The apparatus of claim 1 wherein the housing has a floor level end and a top end, the inlet end being near the top end and the outlet end being near the floor level end.

* * * * *